US006796926B2

United States Patent
Reinkensmeyer et al.

(10) Patent No.: US 6,796,926 B2
(45) Date of Patent: Sep. 28, 2004

(54) MECHANISM FOR MANIPULATING AND MEASURING LEGS DURING STEPPING

(75) Inventors: David J. Reinkensmeyer, Irvine, CA (US); John H. Wynne, III, Long Beach, CA (US)

(73) Assignee: The Regents of the University of California, Oakland, CA (US)

( * ) Notice: Subject to any disclaimer, the term of this patent is extended or adjusted under 35 U.S.C. 154(b) by 223 days.

(21) Appl. No.: 10/226,494

(22) Filed: Aug. 22, 2002

(65) Prior Publication Data

US 2003/0064869 A1 Apr. 3, 2003

Related U.S. Application Data

(60) Provisional application No. 60/314,332, filed on Aug. 22, 2001.

(51) Int. Cl.$^7$ ................................ A63B 22/00
(52) U.S. Cl. ................ 482/8; 482/51; 601/33
(58) Field of Search ............... 482/1–9, 51, 52, 482/54, 57, 60, 61, 900, 66, 69–71; 601/23, 33–35

(56) References Cited

U.S. PATENT DOCUMENTS

| | | | |
|---|---|---|---|
| 6,053,847 A | 4/2000 | Stearns et al. | |
| 6,217,486 B1 | 4/2001 | Rosenow | |
| 6,447,428 B1 * | 9/2002 | McKillip | 482/57 |
| 6,454,682 B1 * | 9/2002 | Kuo | 482/52 |
| 6,575,877 B2 * | 6/2003 | Rufino et al. | 482/51 |

* cited by examiner

Primary Examiner—Glenn E. Richman
(74) Attorney, Agent, or Firm—Fulbright & Jaworski (57) ABSTRACT

A backdriveable device for manipulating and measuring limb movement, and a method of use thereof. The device comprises a plurality of forcers, at least one linear guide for constraining the forcers to reciprocate along respective linear trajectories, and a linkage for attachment to a limb of a user, the linkage rotatably connected between the forcers and including two bars rotatably connected together at a vertex. Movement of the forcers along their linear trajectories results in movement of the vertex along a spatial trajectory. In specific embodiments, the forcers are moving coils of a linear motor. The movement and forces applied by the coils can be controlled through a computer interface, providing robotic control of limb movement.

23 Claims, 8 Drawing Sheets

MECHANISM FOR MANIPULATING AND MEASURING LEGS DURING STEPPING

CROSS-REFERENCE TO RELATED APPLICATIONS

This application is based on provisional application No. 60/314,332, filed on Aug. 22, 2001.

BACKGROUND

1. Field of Invention

This invention relates generally to a mechanism for manipulating and measuring limb movement, and in particular to a programmable, backdriveable device for locomotion training and assessment.

2. Related Art

Mechanisms for manipulating limbs and measuring limb movement have general utility in applications such as athletic training, orthopaedic rehabilitation, virtual reality, and scientific investigation. For patients who cannot walk as a result of traumatic spinal cord injury or stroke, devices that control and measure limb movement provide a means of precisely controlling locomotion training to take advantage of a relatively new rehabilitative technique called "body weight supported locomotion training."This technique involves suspending a spinal cord injured patient in a harness above a treadmill and assisting the patient's legs to move in a walking pattern. The underlying scientific basis for this new technique is the observation that after a complete thoracic spinal cord transection, the hindlimbs of cats can be trained to fully support their weight, rhythmically step in response to a moving treadmill, and adjust their walking speed to that of a treadmill (3,4,7). Results from several laboratories indicate that body weight supported training can also improve stepping in spinal cord injured humans, and that body weight supported training is superior to conventional rehabilitation (2,5).

Current body weight supported training techniques rely on manual assistance to the legs by several therapists to generate the swing phase of stepping and to stabilize the knee during stance. This manual assistance has several important scientific and functional limitations. First, the assistance can vary greatly between therapists and sessions. The patient's ability to step on a treadmill is highly dependent upon the skill level of the persons conducting the training. Second, the therapists can only provide a crude estimate of the required force, torque and acceleration necessary for a prescribed and desired stepping performance. To date, all studies and evaluations of step training using body weight supported training over a treadmill have been limited by the inability to quantify the joint torques and kinematics of the lower limbs during training. This information seems critical to fully assess the changes and progress attributable to step training with the body weight supported training technique. Third, the manual method requires three or four physical therapists to assist the patient during each training session. This labor-intensive protocol is too costly and impractical for widespread clinical applications.

There is a need for a mechanism to assist neurally damaged patients to undergo body weight supported training. Such a mechanism can alleviate the deficiencies inherent in current manual assistance techniques.

An important issue in the design of such a mechanism for movement training is backdriveability, defined as low intrinsic endpoint mechanical impedance, or simply as the ability to move a device by pushing on its linkages. Good backdriveability has several advantages. It allows the patient to move freely when the actuators are not powered. Thus a backdriveable device could record movements of the patient in order to quantify recovery progress. Backdriveable machines can also be made to "fade to nothing" by reducing the amount of assistance they provide as patient recovery improves. Additionally, a backdriveable device can be controlled in such a way that it deviates from a controlled path when the patient exerts uncoordinated forces, providing direct and natural kinematic feedback of movement control errors. In contrast, a non-backdriveable device must rely on force sensing and visual, tactile, or auditory feedback of the sensed force to provide feedback of movement error. A possible safety advantage is that an impedance-controlled, backdriveable machine can "get out of the way" of the patient if the patient rapidly changes his or her pattern of force development. Finally, a backdriveable machine can be designed to record movements and forces applied by therapists, then replay them.

In addition to backdriveability, a mechanism for movement training can benefit from the incorporation of robotic technology. Robotics provides a way to precisely control leg movement during treadmill training and to quantify in real time the kinematics and kinetics of stepping. The application of robotics to locomotion training could ultimately lead to automated treadmill training and monitoring in the clinic, reducing the cost of training and increasing accessibility.

Progress in developing robots for locomotor therapy is being made. The Mechanized Gait Trainer is a singly-actuated mechanism that drives the feet through a gait-like trajectory (6). The device consists of two foot plates connected to a doubled crank and rocker system. An induction motor drives the cranks via a planetary gear system. The rear ends of the foot plates follow an ellipsoid-like movement. Different gears can be incorporated to vary stride length and timing. The planetary gear system also moves the patient harness in a locomotion-like trajectory through two cranks attached to suspension ropes. The torque generated by the motor is sensed and displayed on-line to provide a biofeedback signal to the patient. The device has been used to train two patients who were two months post-stroke. The patients received four weeks of gait training with the device, consisting of five 20-minute sessions per week. The patients improved significantly in their overground walking ability.

The Lokomat is a motorized exoskeleton worn by the patients during treadmill walking (1). This device has four rotary joints that accommodate hip and knee flexion/extension for each leg. The joints are driven by precision ball screws connected to DC motors. Parameters such as the hip width, thigh length, and shank length can be manually adjusted to fit individual patients. The weight of the exoskeleton is supported by a parallelogram mechanism that moves in the vertical direction and is counterbalanced by a gas spring. The hip and knee motors can be programmed to drive the legs along gait-like trajectories. The device is relatively stiff and is difficult for the patient to move under his own power. Therapeutic results have not been reported for the Lokomat, although several spinal cord injured patients have tested the device. The device was able to drive gait-like patterns in the patients, reducing the labor burden on the therapists who were assisting in the step training.

While cleverly designed and useful, these two robotic devices lack backdriveability. The Mechanized Gait Trainer is not fully backdriveable because it cannot be driven away from the path specified by its single degree-of-freedom mechanical linkage. The Lokomat is difficult to backdrive because it uses high-advantage, ball-screw actuators. Backdriveability with substantial actuator power is in general difficult to achieve, although some backdriveability can be endowed to a non-backdriveable device by sensing the contact force between the device and the environment, and moving the actuators in order to control that force. The simplest and most robust approach to good backdriveability, however, remains the minimization of friction and inertia of the mechanism and actuators.

SUMMARY

It is an object of the present invention to incorporate a backdriveable robotic device into locomotion training and assessment The device should be capable of generating substantial forces for assisting in stepping, while minimally encumbering the legs of a patient.

Accordingly, the present invention provides a backdriveable device for measuring and manipulating limb movement. The device comprises a plurality of forcers, at least one linear guide for directing the forcers to move back and forth along their respective linear paths, and a linkage rotatably connected between the forcers and including two bars rotatably connected together to form a vertex. As the forcers move along their linear paths, they apply force to the linkage, resulting in movement of the vertex in a spatial trajectory. For locomotion training, the linkage can be connected at the vertex to a patient's leg by attachment to the lower shank, pelvis, knee, ankle or sole of the foot.

In particular embodiments, the forcers are moving coils of a linear motor. Mounted on a linear bearing, the coils provide substantial force with minimal friction. The movement and forces applied by the coils can be controlled through a computer interface, providing robotic control of limb movement.

The present invention also provides a method of measuring and manipulating limb movement using a backdriveable device. The method comprises: (a) providing a plurality of forcers moving along respective linear paths; (b) rotatably connecting a linkage between the forcers—the linkage includes two bars rotatably connected together at a vertex, and the forcers and linkage are connected such that movement of the forcers along their respective linear trajectories results in movement of the vertex in a spatial trajectory; (c) attaching the linkage to a limb of a user; and (d) moving the plurality of forcers along their respective paths. In practice, movement of the forcers can initiate movement of the limb along a spatial trajectory, or the limb can first move along a spatial trajectory, driving the passively moving forcers along their linear paths.

The backdriveable device of this invention has a number of advantages. For example, when practiced with a moving coil linear motor that generates substantial force with low backdrive friction, the device is powerful yet lightweight. Also, when applied to locomotion training, force application can be mechanically constrained to a physical workspace that matches that of the leg during walking (i.e. horizontally wide but vertically short) with simple hard stops or by installing short links. Another advantage is that in contrast to exoskeletal approaches, the device can accommodate any size leg and any stepping trajectory without mechanical adjustment.

The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION

As used herein, the term "forcer" refers to a component that generates the force applied to a linkage. A linkage can comprise two or more bars. The point were two bars intersect is called a "vertex". The term "apex" refers to a vertex formed by one end of each bar.

The present invention provides a backdriveable exercise device with general applicability to such diverse activities as athletic training, orthopaedic rehabilitation, virtual reality, and general scientific investigations. The device is particularly suitable for manipulating and measuring arm and leg movements. More particularly, it is useful in training patients who have had spinal cord injuries, strokes, or other injuries to walk again, and to measure leg movement during locomotion.

Figure 1:
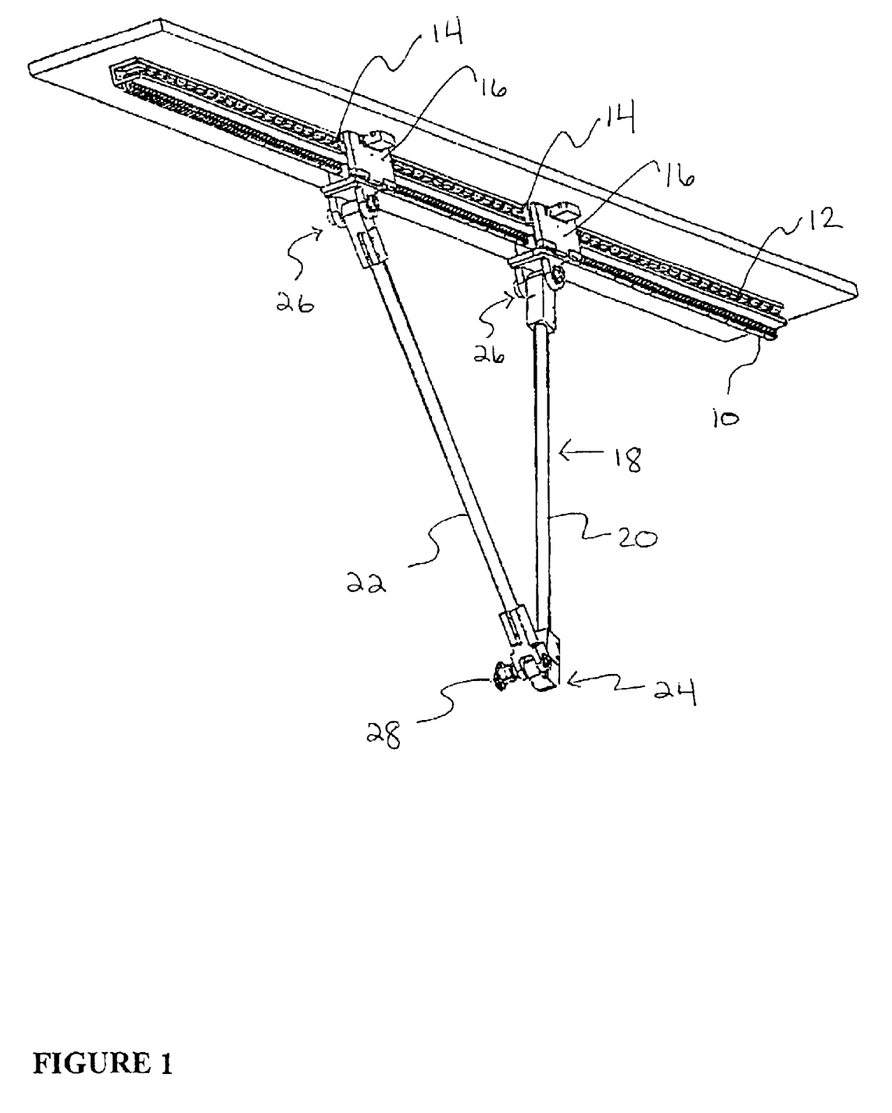
FIG. 1 is a perspective view of a backdriveable device in accordance with the present invention.

Referring to a specific embodiment illustrated in FIG. 1, a low-friction linear bearing 10 is mounted on a magnetic way 12 of a linear motor to guide a pair of moving coils forcers 14 projecting into the magnet way 12. Each coil forcer 14 is slidingly connected to the linear bearing 10 through a respective L-shaped bracket 16. A two-bar linkage 18 is pivotally connected between the coil forcers 14. A pair of bars 20 and 22 constituting the linkage 18 form a V-shape. The bars are rotatably linked at their bottom ends with a rotary bearing to intersect at a vertex, forming an apex 24. The upper end of each bar is pivotally connected through a revolute joint 26 to the respective L-shaped bracket 16. The mounting between the revolute joint and L-shaped bracket can be designed to have some "play" or "springiness" such that the leg of a user can move slightly in and out of the parasagittal plane, as is common in normal walking.

Figure 2:
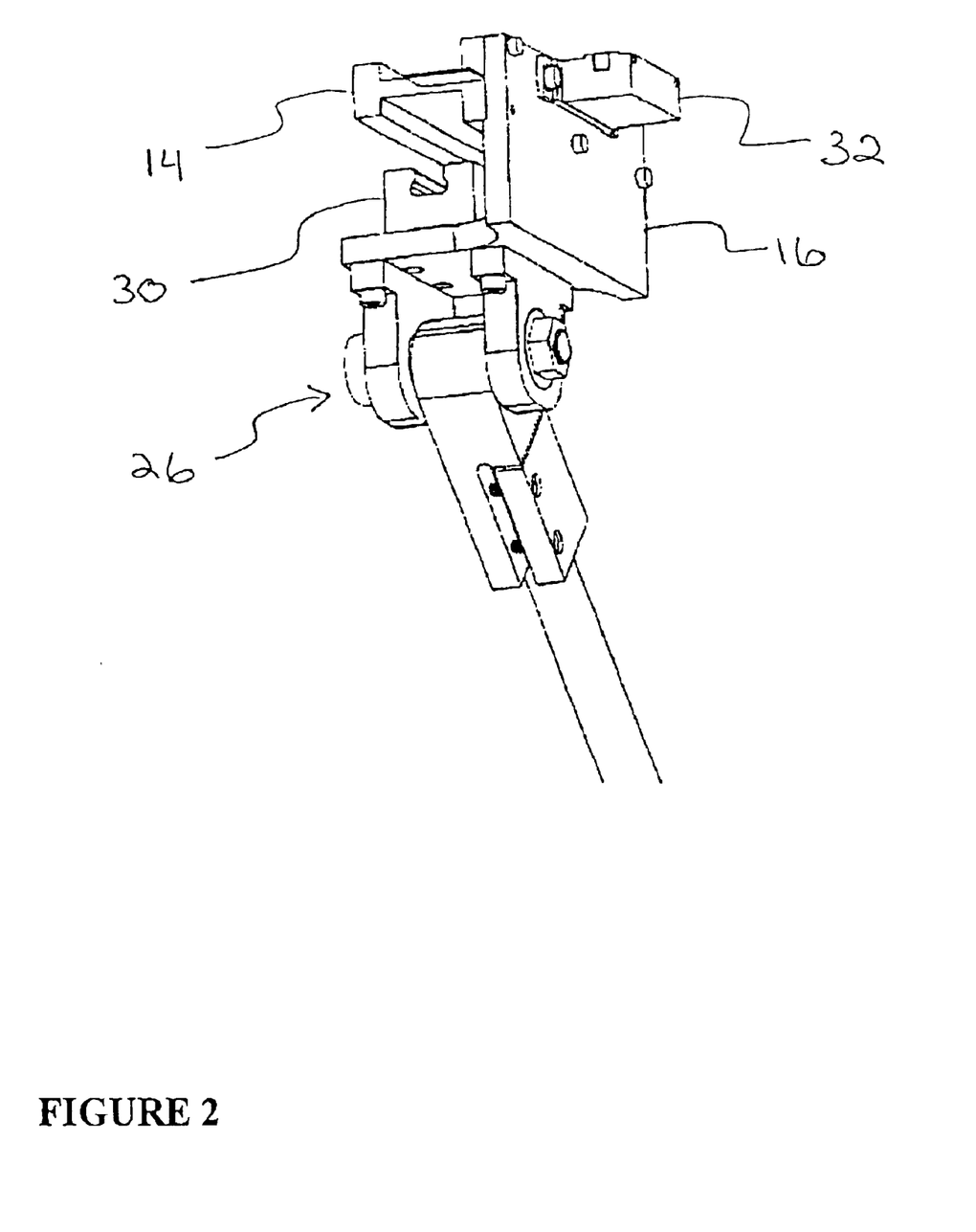
FIG. 2 is a close-up view of a forcer-bracket assembly.

FIG. 2 provides a close-up view of the forcer-bracket assembly. The coil forcer 14 is attached to the inner surface of one arm of the L-shaped bracket 16, and a linear bearing block 30 is attached to the inner surface of the other arm of the L-shaped bracket 16. The coil forcer and linear bearing block are oriented in such a manner that the coil forcer projects into the magnetic way when the linear bearing block engages the linear bearing. The revolute joint 26 is mounted on the outer surface of the L-shaped bracket, opposite the linear bearing block. In addition, a linear encoder 32 is attached to the outer surface of the L-shaped bracket, opposite the coil forcer, although other bracket locations are possible, such as on the inner corner of the L-shaped bracket. The linear encoder senses the position of the forcer-bracket assembly, a function necessary for commutation of the motor as well as for application of kinematic algorithms for calculating the exact position of the apex. A suitable, commercially available linear encoder is the optical non-contact encoder RGH22 from Renishaw, Inc. The encoder can sense position by reflecting light into a graduated optical tape mounted on the magnet way.

Figure 3:
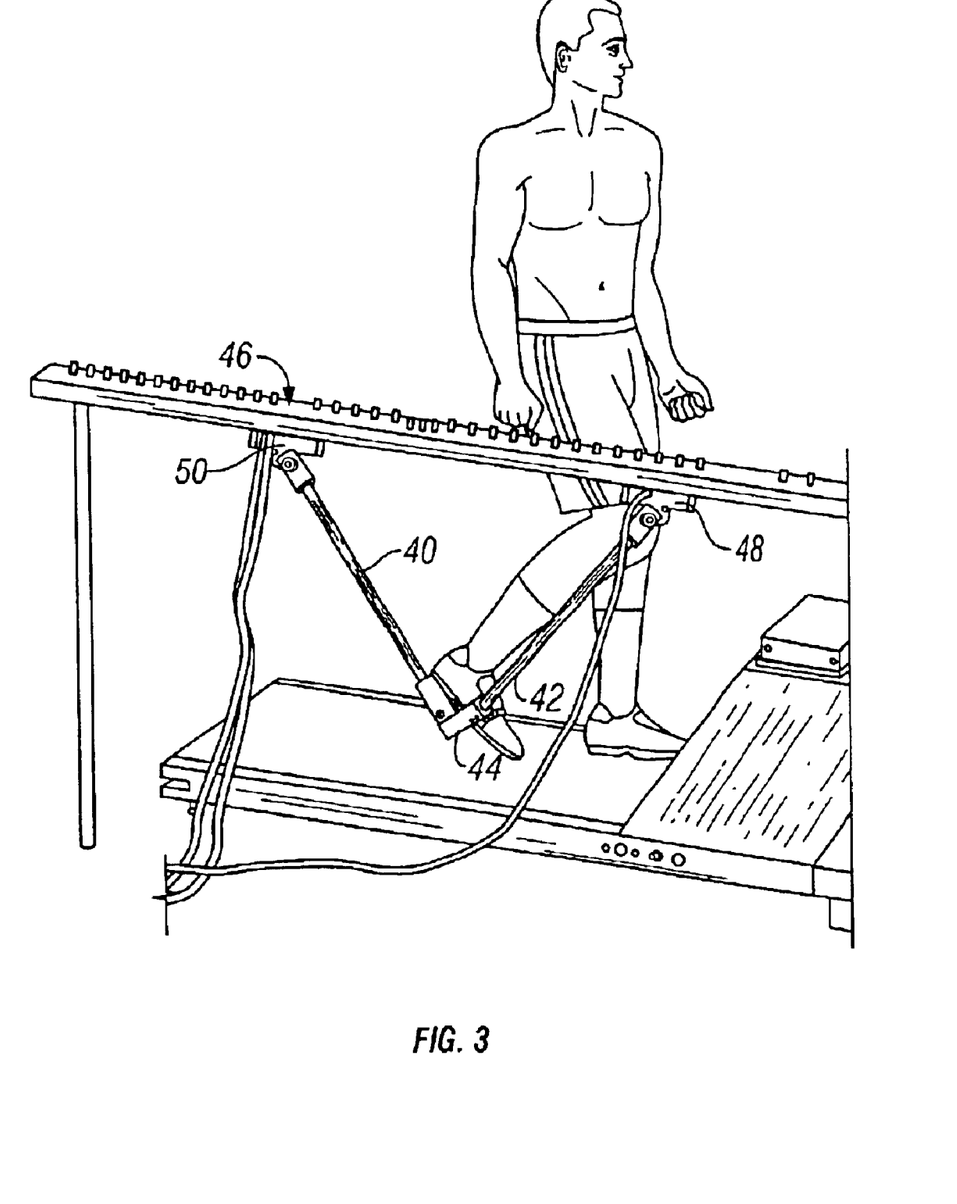
FIG. 3 shows a subject connected to the apex of a backdriveable device having a two-bar linkage.

Referring again to FIG. 1, the apex 24 can be attached to various points on a user's leg by employing a spherical or revolute bearing 28 connected to a suitable attachment device such as a padded, molded plastic cuff for attachment to the lower shank, an orthopaedic brace for attachment to the knee, and a flat plate for attachment to the foot. The apex is connected to the user such that the apex moves in a parasagittal plane. FIG. 3 shows one way of placing a specific embodiment of the present invention. Bars 40 and 42 of the linkage form an apex 44 which is attached to the user's foot. The linear motor-linear bearing assembly 46 is positioned above the linkage with the forcer-bracket assemblies 48 and 50 moving horizontally. In FIG. 3, the user is supporting his own weight. In other applications such as body weight supported training, a user can be suspended from a harness to provide the user with weight support.

Relative linear motion of the coil forcers in opposite directions causes the apex of the two-bar linkage to move in a planar trajectory. The movement and forces applied by the coil forcers are controlled and sensed through a computer interface.

The apex can be moved in any desired planar trajectory $x(t), y(t)$ by moving the forcers along linear trajectories $x_1(t)$ and $x_2(t)$, as specified by:

$$x_1(t)=x(t)+\sqrt{l^2-y^2(t)}$$

$$x_2(t)=x(t)-\sqrt{l^2-y^2(t)}$$

where l is the length of each link. Planar force $F_x$, $F_y$ applied by the apex to the leg can be controlled by applying forces $F_1$ and $F_2$ with the moving coils, as follows:

$$F_1 = 0.5 F_x + \frac{(x_2-x_1)}{4\sqrt{l^2-\left(\frac{x_2-x_1}{2}\right)^2}} F_y$$

$$F_2 = 0.5 F_x - \frac{(x_2-x_1)}{4\sqrt{l^2-\left(\frac{x_2-x_1}{2}\right)^2}} F_y$$

Figure 4:
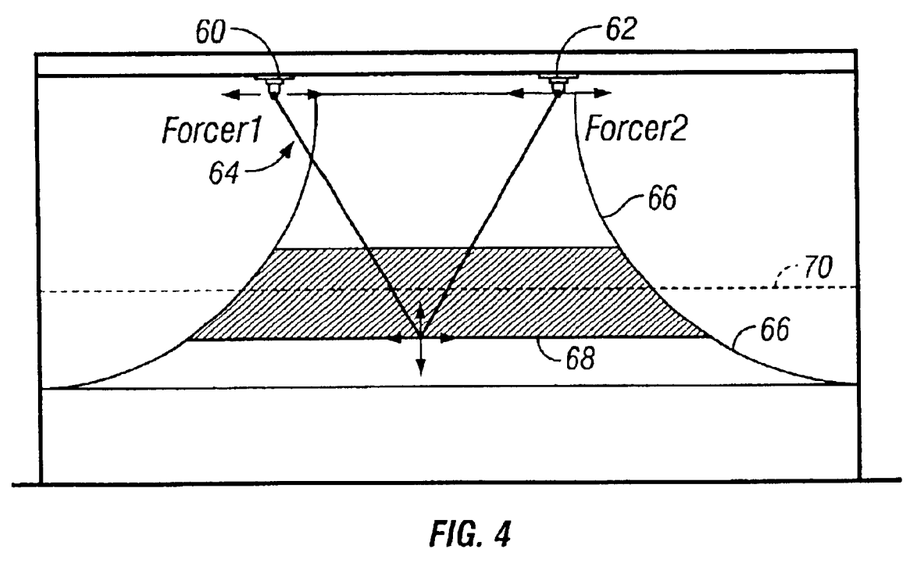
FIG. 4 is a diagram illustrating the workspace of a backdriveable device of the present invention.

In accordance with this invention, a backdriveable device for locomotion training can have a workspace that matches the leg's functional workspace, and the force generation of the device can match the requirements for force development during step training. During walking, a leg moves in a horizontally wide (<1 m) but vertically short (<0.2 m) workspace, and is confined approximately to the parasagittal plane FIG. 4 shows, in diagrammatic format, a side view of a backdriveable device having two moving coil forcers 60 and 62 driving a two bar linkage 64. White area 66 shows the full workspace of the device Shading 68 is the workspace for walking. The workspace of the device can be limited to the shaded area shown in FIG. 4 using simple hard stops on the linkage and linear guide. Below the dashed line 70, the device has mechanical advantage such that the vertical forces that it can generate exceed the sum of the forces that the individual forcers can generate, making possible the application of large vertical forces during stance with minimal linkage encumbrance.

A backdriveable device of the present invention also produces forces that match the requirements of step training. Trainers often push downward on the lower shank during stance in order to increase load-related input to the spinal cord. When the foot is on the ground, the linkage has mechanical advantage in the vertical direction and can generate a vertical force greater than the sum of the linear forces from the moving coils. This allows large loads to be delivered to the foot during stance. During swing, mechanical advantage is decreased, but the forces are still sufficient to lift the leg.

In the specific embodiment shown in FIG. 1, the links are approximately of equal length, providing optimal movement and force. In other embodiments, links of unequal length can be employed. Further, a linkage can be composed of more than two links as long as at least two of the links are rotatably connected together at a vertex.

Additional linkages can be added for attachment to multiple sites of a user's body. As an illustration, a device can have two pairs of moving coils driving two respective V-shaped linkages. One linkage can be longer for attachment to the ankle and the other linkage can be shorter for attachment to the knee. The device can simultaneously provide planar motion control of both ankle and knee. To protect the shank from compressive and tensile forces, an optional rigid link can be attached between the apexes of the linkages.

Figure 5:
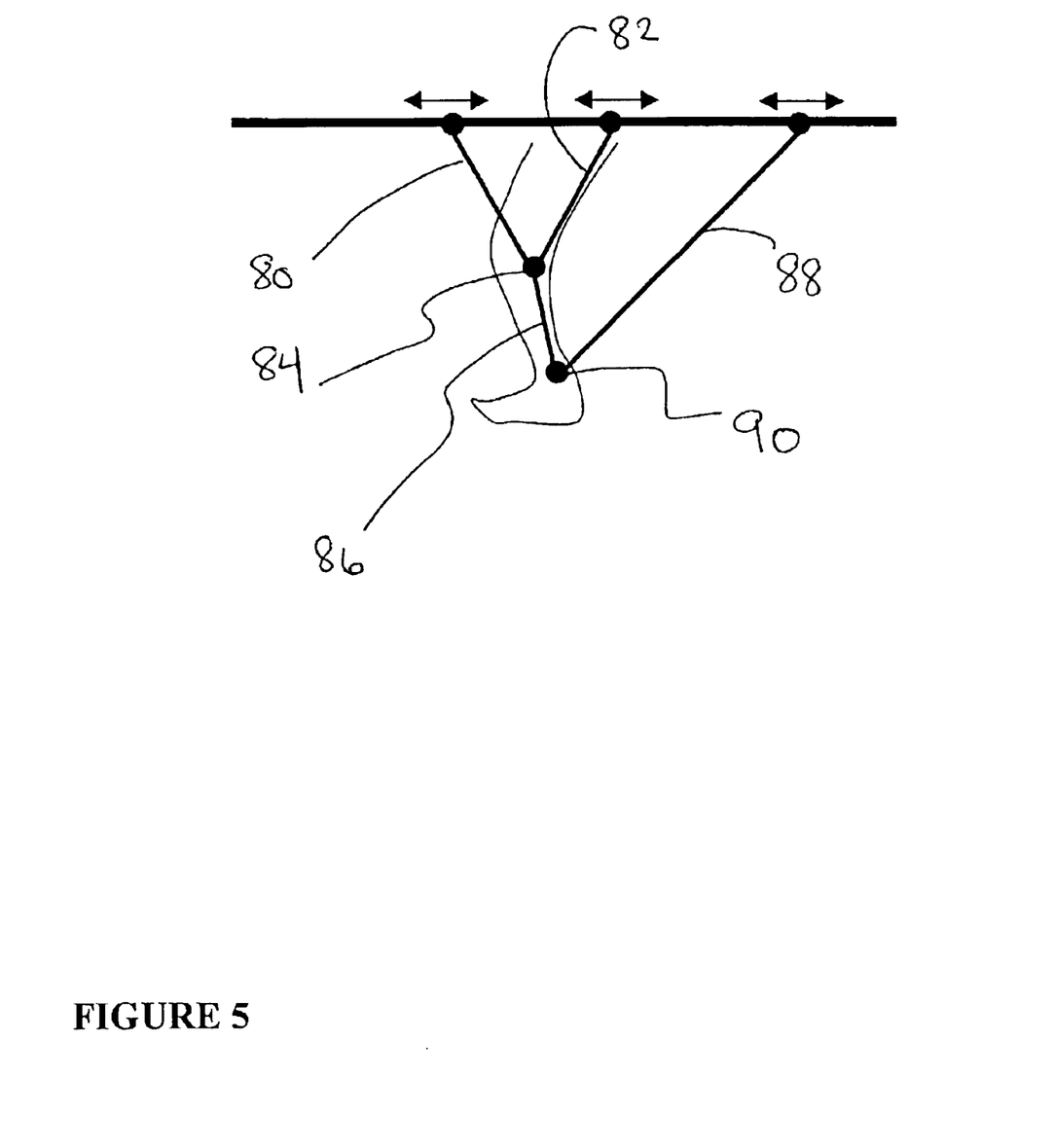
FIG. 5 is a sketch of a backdriveable device for connecting to the ankle and knee of a user.

As a further illustration, a device can have one pair of moving coils with a respective V-shaped linkage for attachment to the knee, and a second, two-bar linkage connected at one end to a third moving coil and at the other end to the apex of the first linkage. The apex of the second linkage can be attached to a different part of the user's body such as the ankle or foot. Referring to an embodiment of such a device shown schematically in FIG. 5, a first V-shaped linkage comprising bars 80 and 82 can be attached by apex 84 to a user's knee. A second linkage, comprising bar 86 connected at one end to apex 84 and bar 88 connected at one end to a moving coil, can be attached by apex 90 to the user's ankle. The device provides simultaneous control of both ankle and knee.

Figure 6:
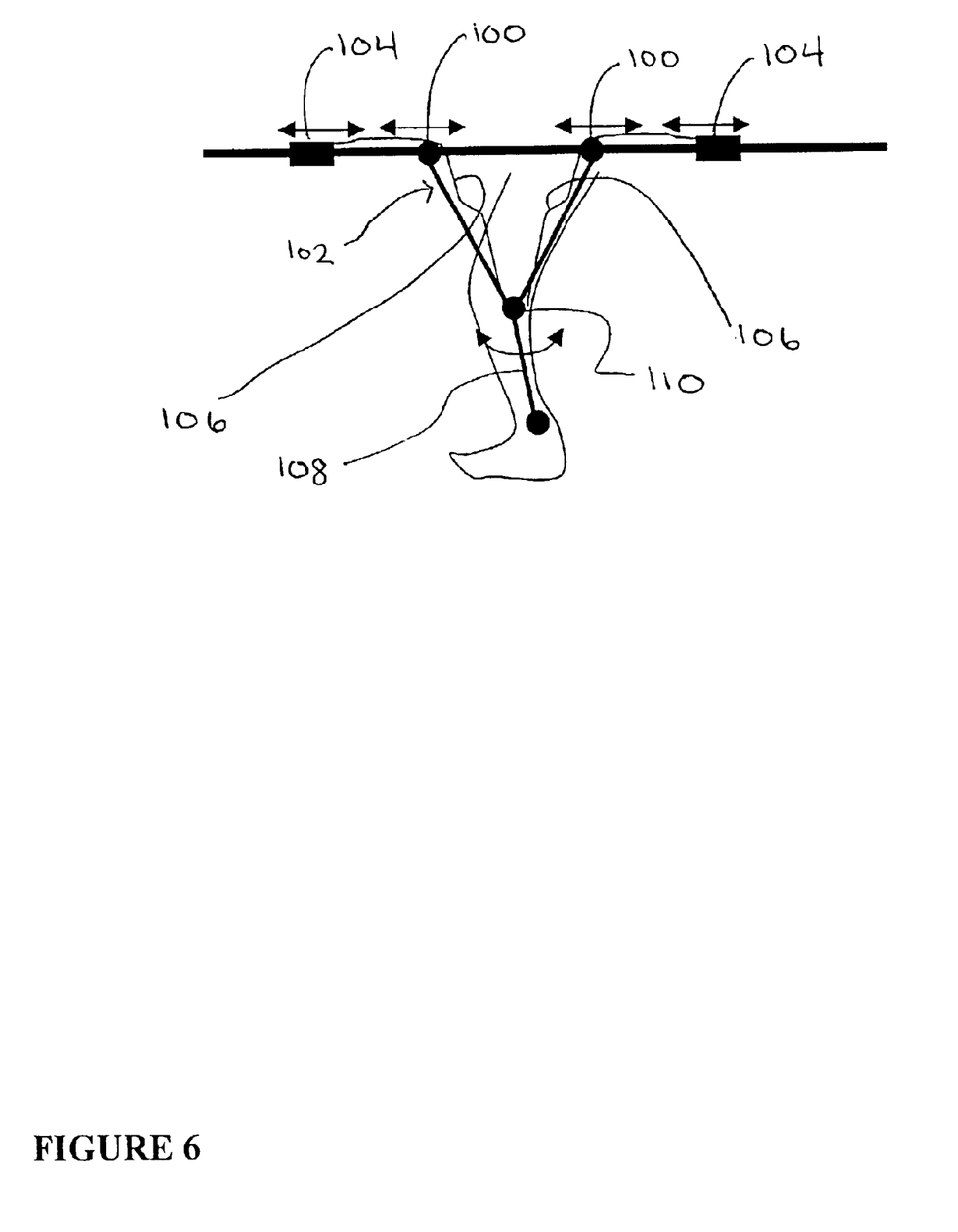
FIG. 6 is a sketch of a backdriveable device for connecting to the lower shank of a user.

In other embodiments, simultaneous control of both ankle and knee can be accomplished by attachment to the lower shank of a user. Referring to a particular embodiment shown schematically in FIG. 6, a pair of moving coils 100 with a respective two-bar V-shaped linkage 102 is connected to a linear guide. A second pair of coils 104 is connected to the same linear guide. Each of the second pair of coils is attached to a cable 106 that wraps around at least at least one pulley revolutely mounted on a coil of the first pair of coils. A third bar 108 is rotatably connected at one end to apex 110 of the V-shaped linkage 102. The cables 106 extend and attach to this end of the third bar such that movement of the second pair of coils causes pulling of the cables, resulting in rotation of the third link. The third link can be attached to the lower shank for control of both position and orientation of the lower shank. This is equivalent to planar control of both knee and ankle.

The specific embodiment shown in FIG. 1 has forcers moving horizontally above the linkage. Other configurations are possible such as flipping the device upside down with the forcers moving horizontally below the linkage, and flipping the device sideways with the forcers moving vertically. Such configurations can provide more compact designs with shorter linkages.

Although the invention is preferably practiced with a linear motor, other ways of moving the forcers, such as use of a rotary motor attached to pulley and cable systems or use of a rotary motor with lever arms attached to the forcers, are well known in the art.

Each forcer of the present invention moves along a linear trajectory. Both forcers of a linkage can move along the same trajectory by sharing a single linear guide, as shown for the device in FIG. 1. Alternatively, the forcers can move along collinear, parallel or skewed linear trajectories by using separate linear guides whose longitudinal axes are collinear, parallel or skewed, respectively, to each other.

In further embodiments of the present invention, a third degree-of-freedom can be added to provide movement perpendicular to the parasagittal plane. This third degree-of-freedom can be powered, providing a backdriveable device moving in three dimensions. To illustrate, a first linear guide can be placed parallel to a second linear guide having a pair of coil forcers with a respective V-shaped linkage, and a link from a coil forcer on the first linear guide can be attached to the apex of the second guide's V-shaped linkage. Alternately, a rotary motor can rotate a linear bearing such that a V-shaped linkage associated with the linear bearing moves perpendicular to the parasagittal plane. A force sensor can be interposed between the linkage vertex and the limb to measure contact forces therebetween, allowing the device to quantify and then replay the measured contact forces.

The present invention may be better understood by referring to the following examples.

EXAMPLE 1

This example shows how to assess the backdriveability of a device of the present invention. In accordance with the specific embodiment shown in FIG. 1, moving coil forcers having a mass of 0.32 kg and a peak force of 17.6 kg were employed. The positions of the moving coils were measured using a linear optical encoder with two read heads. The movement and applied force of the forcers were controlled using a commercially available program, Real Time Windows Target (The MathWorks, Inc.), running on a PC compatible computer. Key properties of the device are shown in Table 1.

TABLE 1

| KEY PROPERTIES | |
|---|---|
| Maximum continuous force | 116 N* |
| Peak force | 285 N* |
| Workspace | 127 cm wide at the treadmill surface |
| | 77 cm at 20 cm above the treadmill surface |
| Backdrive friction | 3.4 N* |
| Position measurement resolution | .005 mm* |
| Maximum simulated stiffness | >8.8 N/mm* |
| Maximum simulated viscosity | >.53 N/mm/s* |

*values at apex angle of 45° (5.5 cm above treadmill)

Figure 7:
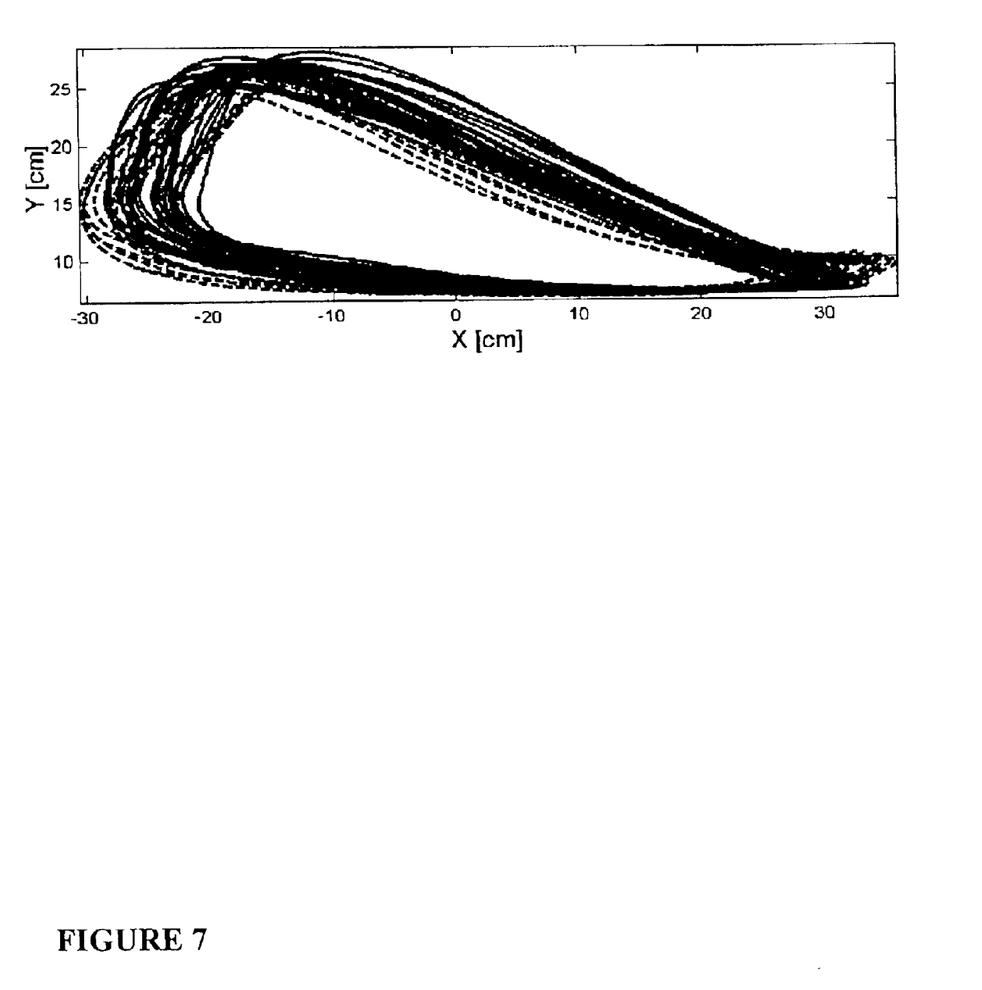
FIG. 7 shows stepping trajectories of a subject with and without an attached backdriveable device.

To assess the backdriveability of the device, stepping trajectories of an unimpaired subject stepping on a treadmill at 0.9 m/s were measured. The device was attached to the subject's foot with a platform connected to the bottom of the user's shoe. The device did not apply assistive forces during stepping. Instead, the device's linkage moved passively with the subject's foot. For comparison, the subject also stepped without the device attached to the bottom of the foot. In both cases, the planar motion of the ankle was measured using a low friction (<0.2 N) mechanical digitizer. The results are shown in FIG. 7, which is a graph of horizontal (X) and vertical (Y) ankle positions. Stepping trajectories with the device attached are shown in solid lines and stepping trajectories without the device are shown in dashed lines. In the figure, twenty trajectories are shown for each condition. The stepping trajectories were similar with and without the device attached, with small differences at toe off and heel strike.

EXAMPLE 2

To test the ability of the backdriveable device of Example 1 to assist in stepping, stepping trajectories from the unimpaired subject at 0.9 m/s on the treadmill were recorded using the backdriveable device. The trajectories were then actively tracked with a proportional-derivative position controller. The device reproduced the recorded steps with a mean tracking error of 3 mm.

EXAMPLE 3

This example shows how to measure movement adaptation induced by the backdriveable exercise device during locomotion activity. For studies of motor control, Shadmehr and Mussa-Ivaldi developed a useful protocol in which a backdriveable robotic apparatus applied a perturbing force-field to the hands of unimpaired subjects as they reached (8). The forces initially curved the reaching path of the hand (the "direct-effect"), but the subjects straightened their hand paths with practice. When the forces were unexpectedly removed, the resulting hand path was displaced in the direction opposite the force. The presence of this "after-effect" or adaptation is evidence that the nervous system used an internal model of the arm and its environment to compensate for the force-field. Numerous subsequent studies with robots have provided insight into the use of internal models.

Figure 8:
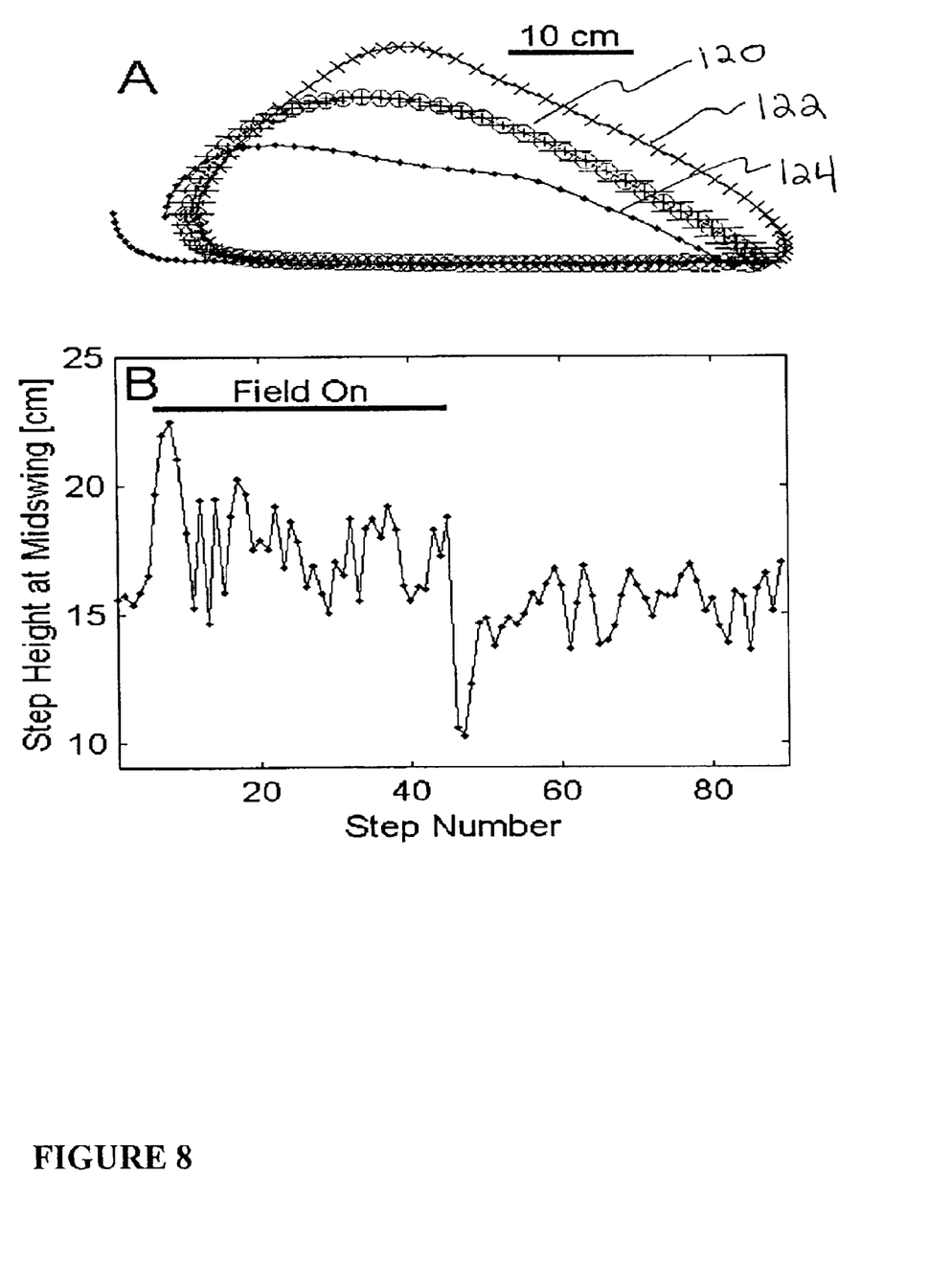
FIG. 8A shows stepping trajectories under different force-field conditions.
FIG. 8B is a graph showing step height during and after force field application.

Movement adaptation induced by the device of Example 1 was tested in a simple force-field experiment. The device applied an upward force that depended on the forward horizontal velocity of the subject's foot:

$$F_y = B\dot{x} \quad \dot{x} > 0$$

$$F_y = 0 \quad \dot{x} \leq 0$$

with B=26 Ns/m. The subject stepped for 90 steps. The force field was applied unexpectedly after twenty steps, then removed after 40 more steps. FIG. 8A shows the stepping trajectories recorded by the device in the force-field experiment. A recording 120 with open circles indicates a mean (plus or minus one standard deviation) step trajectory for the five steps in the null field preceding application of the force field. A recording 122 with crosses indicates a mean step trajectory when the force field was applied. A recording 124 with filled circles indicates a mean step trajectory after the force field was removed. FIG. 8B is a graph of step height at midswing versus step number, showing: direct-effect when the force field is applied (steps 5–8); learning curves during application of the force field (steps 8–45); after-effect when the field is removed (steps 46–47); and wash-out of the after-effect (steps 48–60). The results demonstrate that the subject exhibited a direct-effect when the force field was applied and an after-effect when the force field was removed.

REFERENCES

The following publications are hereby incorporated by reference:
1. Colombo G, Joerg M, Schreier R, Dietz V: Treadmill training of paraplegic patients with a robotic orthosis *J Rehab Res Dev* 37(6): 693–700, 2000.
2. Dobkin, B. H., Harkema, S., Requejo, P., and Edgerton, V. R. Modulation of locomotor-like EMG activity in subjects with complete and incomplete spinal cord injury. *J. Neuro. Rehab.* 9: 183–190, 1995.
3. Edgerton et al., Recovery of full weight-supporting locomotion of the hindlimbs after complete thoracic spinalization of adult and neonatal cats. In: *Restorative Neurology, Plasticity of Motoneuronal Connections*. New York, Elsevier Publishers, 1991, pp. 405–418.
4. Edgerton, et al., Does motor learning occur in the spinal cord? *Neuroscientist* 3:287–294, 1997.
5. Harkema, S. J., Hurley, S. L., Patel, U. K., Requejo, P. S., Dobkin, B. H., and Edgerton, V. R. Human lumbosacral spinal cord interprets loading during stepping. *J. Neurophysiol.* 77: 797–811, 1997.
6. Hesse S, Uhlenbrock D: A mechanized gait trainer for restoration of gait *J Rehab Res Dev* 37(6):701–8, 2000.
7. Hodgson, et al., Can the mammalian lumbar spinal cord learn a motor task? *Med. Sci. Sports Exerc.* 26:1491–1497, 1994.
8. R. Shadmehr and F. A. Mussa-Ivaldi, "Adaptive representation of dynamics during learning of a motor task," *Journal of Neuroscience, vol.* 14, pp. 3208–3224, 1994.

What is claimed is:

1. A backdriveable device for manipulating and/or measuring limb movement, comprising:
   a plurality of forcers;
   at least one linear guide for constraining the forcers to reciprocate along respective linear trajectories, each forcer slidingly connected to said at least one linear guide; and
   a linkage for attachment to a limb of a user, the linkage rotatably connected between the forcers and including two bars rotatably connected together at a vertex, whereby movement of the forcers along their linear trajectories results in movement of the vertex along a spatial trajectory.

2. The device of claim 1 in which each forcer is a moving coil of a linear motor.

3. The device of claim 1 in which the bars are rotatably connected together to form an apex.

4. The device of claim 1 in which the linkage is a two-bar linkage.

5. The device of claim 1 in which said at least one linear guide is at least one linear bearing.

6. The device of claim 1 in which said at least one linear guide is a single linear guide to which the plurality of forcers is slidingly connected.

7. The device of claim 1 in which said at least one linear guide is at least two linear guides having collinear longitudinal axes, wherein each guide is connected to at least one forcer.

8. The device of claim 1 in which said at least one linear guide is at least two linear guides having parallel longitudinal axes, wherein each guide is connected to at least one forcer.

9. The device of claim 1 in which said at least one linear guide is at least two linear guides having skewed longitudinal axes, wherein each guide is connected to at least one forcer.

10. The device of claim 1 in which the linkage is pivotally connected between the forcers such that movement of the forcers along their linear trajectories results in movement of the vertex along a vertically planar trajectory.

11. A backdriveable device for manipulating and/or measuring locomotion, comprising:
    a linear bearing;
    a pair of moveable coils of a linear motor, each coil slidingly connected to the linear bearing; and
    a two-bar linkage for attachment to a leg of a user, the linkage connected pivotally between the coils, each bar of the linkage rotatably connected to the other to form an apex, whereby movement of the coils along the linear bearing results in movement of the apex along a vertically planar trajectory.

12. The device of claim 11, further comprising:
    a second pair of moveable coils slidingly connected to the linear bearing; and
    a second two-bar linkage for attachment to a different part of the same leg, the second linkage connected pivotally between the second pair of coils, each bar of the linkage rotatably connected to the other to form an apex, whereby simultaneous movement of both pairs of coils results in simultaneous movement of both apexes.

13. The device of claim 11 further comprising:
    a third moveable coil slidingly connected to the linear bearing; and
    a second two-bar linkage for attachment to a different part of the same leg, the second linkage connected pivotally between the third moveable coil and the apex of the first two-bar linkage, each bar of the second linkage rotatably connected to the other to form an apex, whereby simultaneous movement of the three coils results in simultaneous movement of both apexes.

14. The device of claim 11 further comprising:
    a second pair of moveable coils slidingly connected to the linear bearing;
    a plurality of pulleys at least one of which is mounted on each coil of the first pair of coils;
    a third bar for attachment to the lower shank of the leg, the bar rotatably connected at one end to the apex of the two-bar linkage; and
    two cables, each connected to a respective coil of the second pair of coils and wrapping around one or more pulleys mounted on a respective coil of the first pair of coils, the cables attached to the rotatably connected end of the third bar such that pulling on the cables by moving the second pair of coils results in rotation of the third bar relative to the apex of the two-bar linkage.

15. A method of manipulating limb movement, comprising:
    providing a plurality of forcers reciprocating along respective linear trajectories;
    rotatably connecting a linkage between the forcers, said linkage including two bars rotatably connected together at a vertex, so that movement of the forcers along their respective linear trajectories results in movement of the vertex in a spatial trajectory;
    attaching the linkage to a limb of a user; and
    moving the forcers along their respective linear trajectories.

16. The method of claim 15 in which the linkage is attached at the vertex to the user's limb.

17. The method of claim 15 in which movement of the forcers is initiated by first moving the attached limb along a spatial trajectory.

18. The method of claim 15 in which moving the forcers initiates movement of the attached limb along a spatial trajectory.

19. A method of measuring limb movement comprising the method of claim 15 and further comprising determining the position of the attached limb as it moves along a spatial trajectory.

20. A method of manipulating stepping, comprising:
 providing a pair of moveable coils of a linear motor;
 pivotally connecting a two-bar linkage between the coils, each bar of the linkage rotatably connected to the other to form an apex, so that movement of the coils along the linear motor results in movement of the apex along a vertically planar trajectory;
 attaching the apex to a leg of a user; and
 moving the coils along the linear motor.

21. The method of claim 20 in which movement of the coils is initiated by first moving the attached leg along a vertically planar trajectory.

22. The method of claim 20 in which moving the coils initiates movement of the attached leg along a vertically planar trajectory.

23. A method of measuring leg movement comprising the method of claim 20 and further comprising determining the position of the attached leg as it moves along a vertically planar trajectory.

* * * * *